United States Patent
Sato et al.

[11] Patent Number: 5,911,687
[45] Date of Patent: Jun. 15, 1999

[54] WIDE AREA MEDICAL INFORMATION SYSTEM AND METHOD USING THEREOF

[75] Inventors: Shinichi Sato, Yamato; Koichi Sano, Yokohama, both of Japan

[73] Assignee: Hitachi, Ltd., Tokyo, Japan

[21] Appl. No.: 08/747,681

[22] Filed: Nov. 12, 1996

[30] Foreign Application Priority Data

Nov. 15, 1995 [JP] Japan ..................................... 7-296477

[51] Int. Cl.$^6$ ...................................................... A61B 5/00
[52] U.S. Cl. ............................................................. 600/300
[58] Field of Search .................................... 600/300, 301; 128/903, 904; 705/2, 3

[56] References Cited

U.S. PATENT DOCUMENTS

| 5,553,609 | 9/1996 | Chen et al. | 600/301 |
| 5,619,991 | 4/1997 | Sloane | 600/300 |

FOREIGN PATENT DOCUMENTS

| 2-218336 | 8/1990 | Japan . |
| 3-198832 | 8/1991 | Japan . |
| 4-15035 | 1/1992 | Japan . |

*Primary Examiner*—Cary E. O'Connor
*Assistant Examiner*—Eric F. Winakur
*Attorney, Agent, or Firm*—Antonelli, Terry, Stout & Kraus, LLP

[57] ABSTRACT

The present invention is a wide area medical information system and a method using thereof comprising a wide area network, a plurality of doctor terminals and patient terminals connected to the wide area network, and a management server including at least an electronic case record file storing clinic information for patient's and a doctor database storing data of a plurality of doctors, wherein the system searches the doctor database on the basis of patient information including the condition of the disease of a certain patient input from the patient terminal, selects the corresponding doctor, requests that the selected doctor take charge of examination and treatment for the aforementioned certain patient, registers the correspondence between the approved doctor and the aforementioned certain patient in the electronic case record file, gives the right to access the clinic information of the patient to the approved doctor, and executes the online examination and treatment via the doctor terminal and patient terminal, so that a patient existing in a wide area can receive remote examination and treatment services of high satisfaction and medical treatment related services other than examination and treatment without depending on the location.

5 Claims, 15 Drawing Sheets

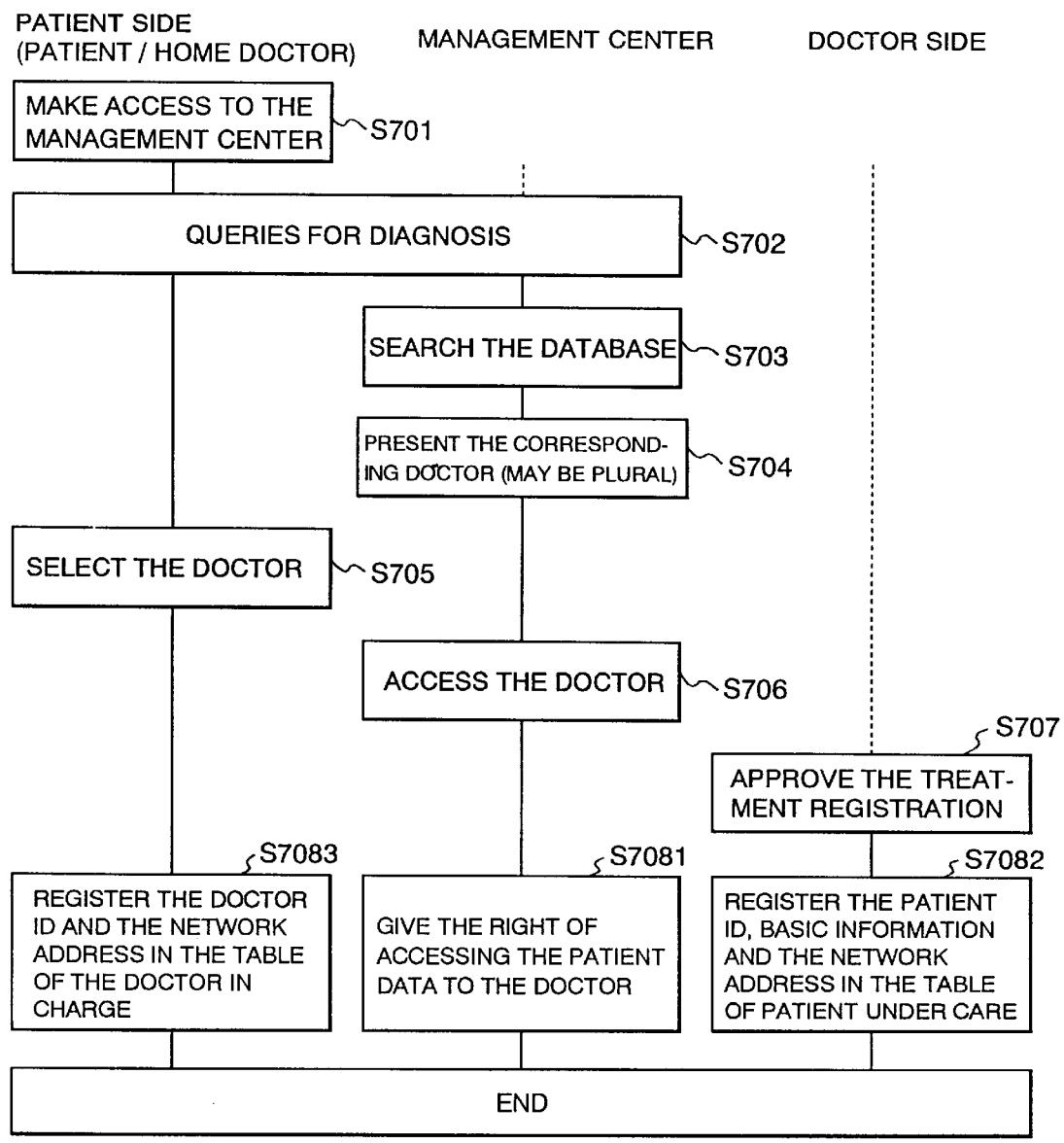

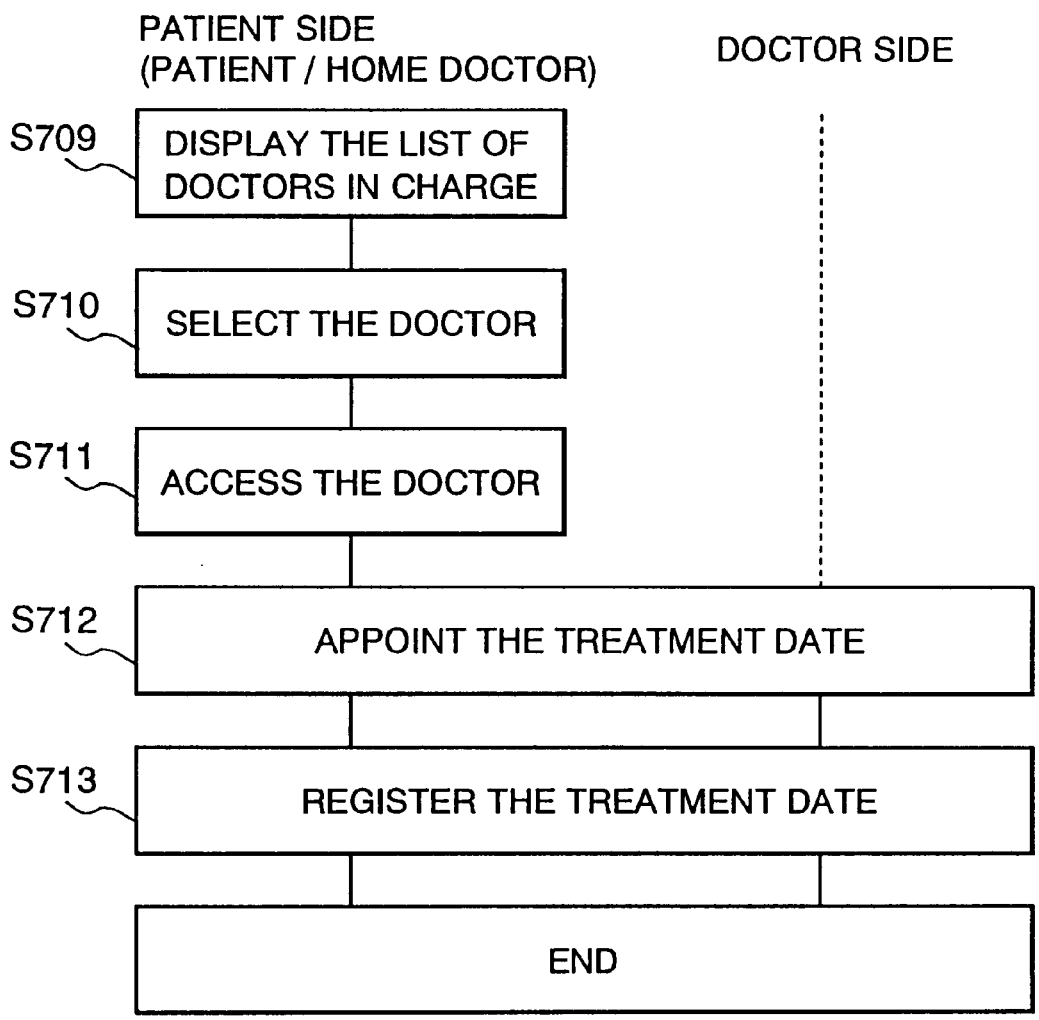

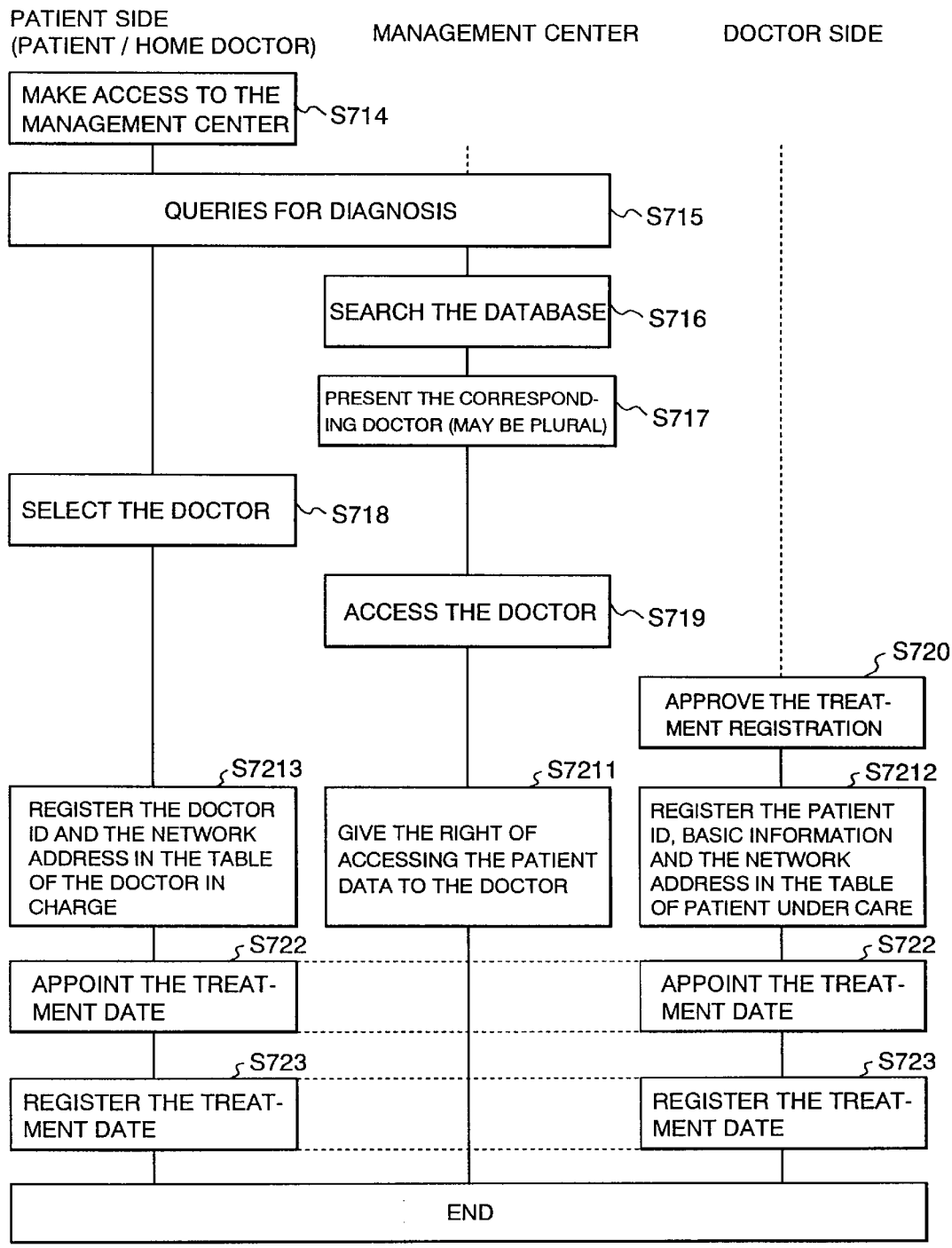

FIG. 10

| DOCTOR'S NAME | CODE | WHERE TO BELONG | LOCATION | SECTION | SPECIALITY | HISTORY | . . . |
|---|---|---|---|---|---|---|---|
| DOCTOR'S NAME 1 | CODE 1 | WHERE TO BELONG 1 | LOCATION 1 | SECTION 1 | SPECIALITY 1 | HISTORY 1 | . . . |
| DOCTOR'S NAME 2 | CODE 2 | WHERE TO BELONG 2 | LOCATION 2 | SECTION 2 | SPECIALITY 2 | HISTORY 2 | . . . |
| DOCTOR'S NAME 3 | CODE 3 | WHERE TO BELONG 3 | LOCATION 3 | SECTION 3 | SPECIALITY 3 | HISTORY 3 | . . . |
| DOCTOR'S NAME 4 | CODE 4 | WHERE TO BELONG 4 | LOCATION 4 | SECTION 4 | SPECIALITY 4 | HISTORY 4 | . . . |

FIG. 11

| DOCTOR CODE | DOCTOR NETWORK ADDRESS | PATIENT CODE | PATIENT NETWORK ADDRESS |
|---|---|---|---|
| DOCTOR CODE 1 | NETWORK ADDRESS 1 | PATIENT CODE 11 | NETWORK ADDRESS 11 |
| DOCTOR CODE 1 | NETWORK ADDRESS 1 | PATIENT CODE 12 | NETWORK ADDRESS 12 |
| . . . | . . . | . . . | . . . |
| DOCTOR CODE 2 | NETWORK ADDRESS 2 | PATIENT CODE 21 | NETWORK ADDRESS 21 |
| DOCTOR CODE 2 | NETWORK ADDRESS 2 | PATIENT CODE 22 | NETWORK ADDRESS 22 |
| . . . | . . . | . . . | . . . |

FIG. 12

| PATIENT CODE | PATIENT'S NAME | AGE | SEX | NETWORK ADDRESS | APPOINTED DATE AND TIME |
|---|---|---|---|---|---|
| PATIENT CODE 1 | PATIENT'S NAME 1 | AGE 1 | SEX 1 | NETWORK ADDRESS 1 | APPOINTED DATE AND TIME 1 |
| PATIENT CODE 2 | PATIENT'S NAME 2 | AGE 2 | SEX 2 | NETWORK ADDRESS 2 | APPOINTED DATE AND TIME 2 |
| PATIENT CODE 3 | PATIENT'S NAME 3 | AGE 3 | SEX 3 | NETWORK ADDRESS 3 | APPOINTED DATE AND TIME 3 |
| PATIENT CODE 4 | PATIENT'S NAME 4 | AGE 4 | SEX 4 | NETWORK ADDRESS 4 | APPOINTED DATE AND TIME 4 |

FIG. 13

| DOCTOR CODE | DOCTOR'S NAME | SECTION | NETWORK ADDRESS | APPOINTED DATE AND TIME |
|---|---|---|---|---|
| DOCTOR CODE 1 | DOCTOR'S NAME 1 | SECTION 1 | NETWORK ADDRESS 1 | APPOINTED DATE AND TIME 1 |
| DOCTOR CODE 2 | DOCTOR'S NAME 2 | SECTION 2 | NETWORK ADDRESS 2 | APPOINTED DATE AND TIME 2 |
| DOCTOR CODE 3 | DOCTOR'S NAME 3 | SECTION 3 | NETWORK ADDRESS 3 | APPOINTED DATE AND TIME 3 |
| DOCTOR CODE 4 | DOCTOR'S NAME 4 | SECTION 4 | NETWORK ADDRESS 4 | APPOINTED DATE AND TIME 4 |

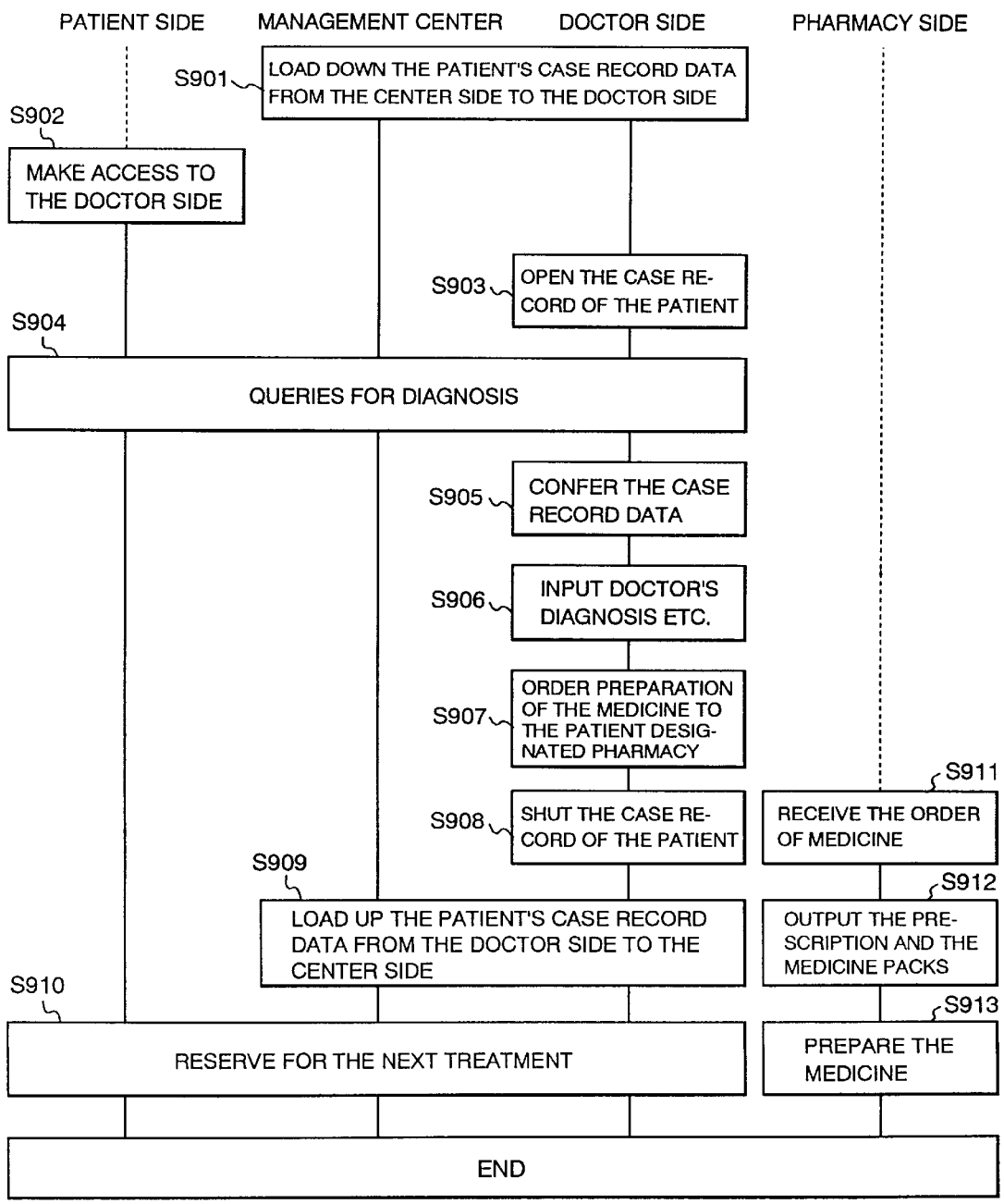

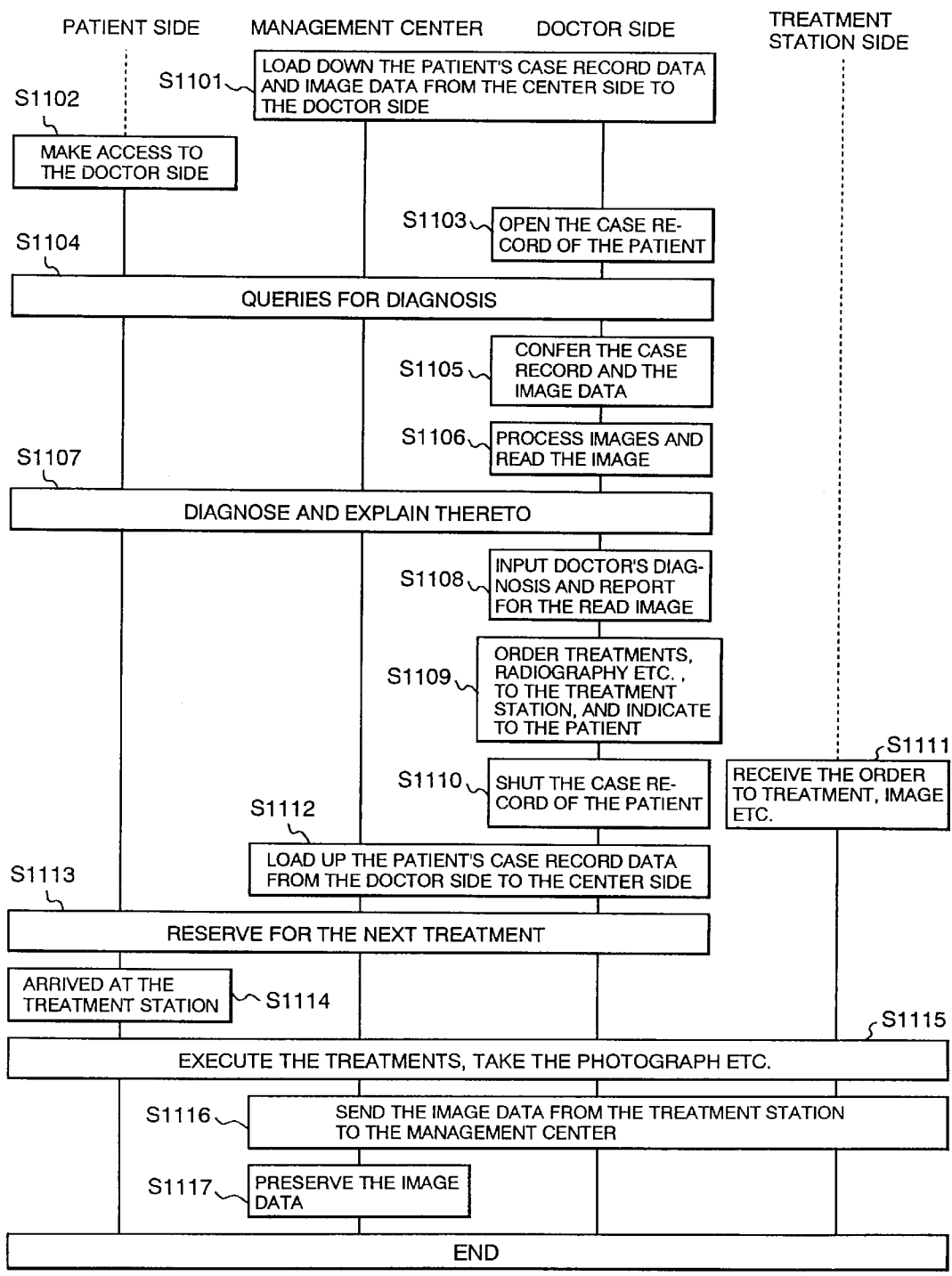

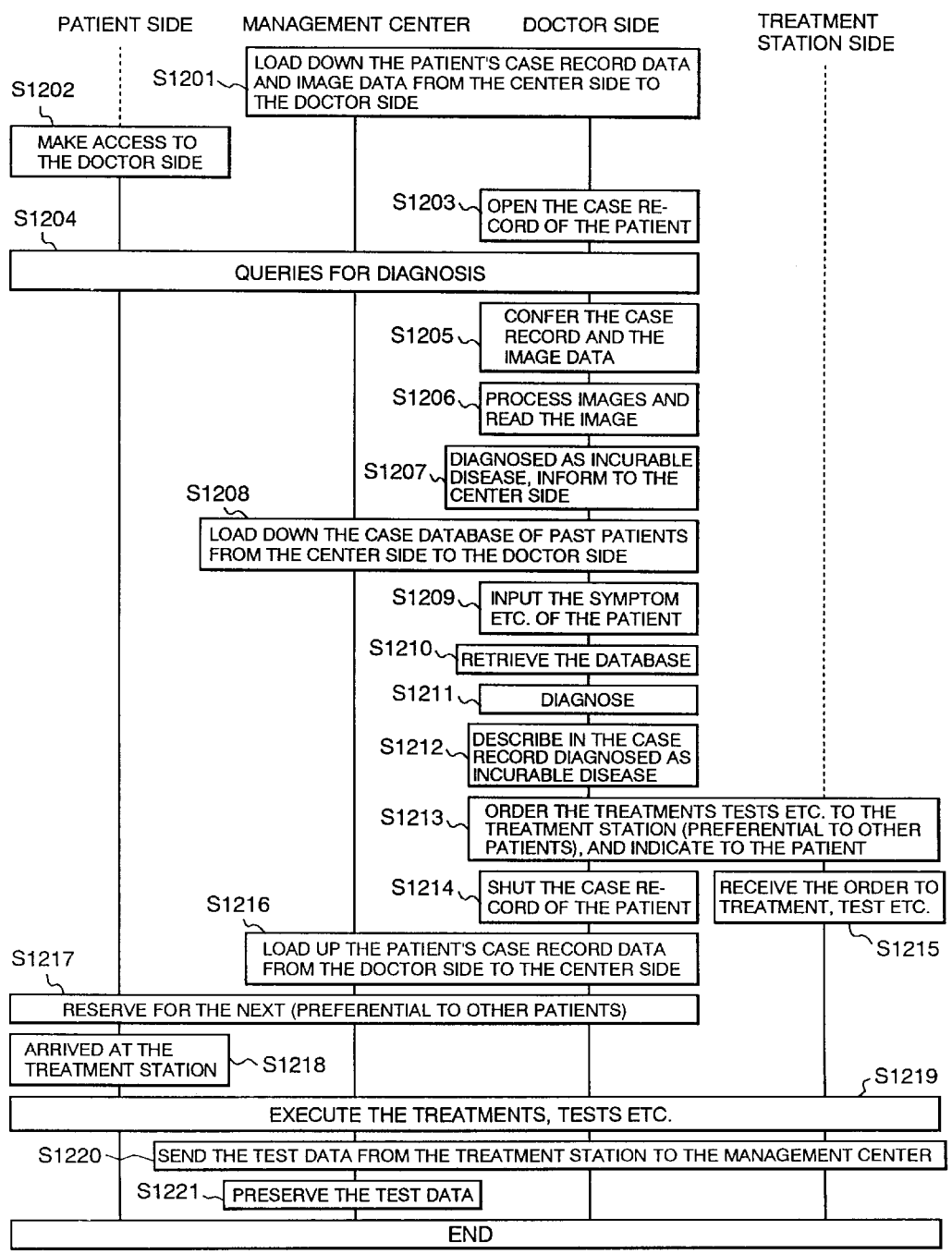

FIG. 18

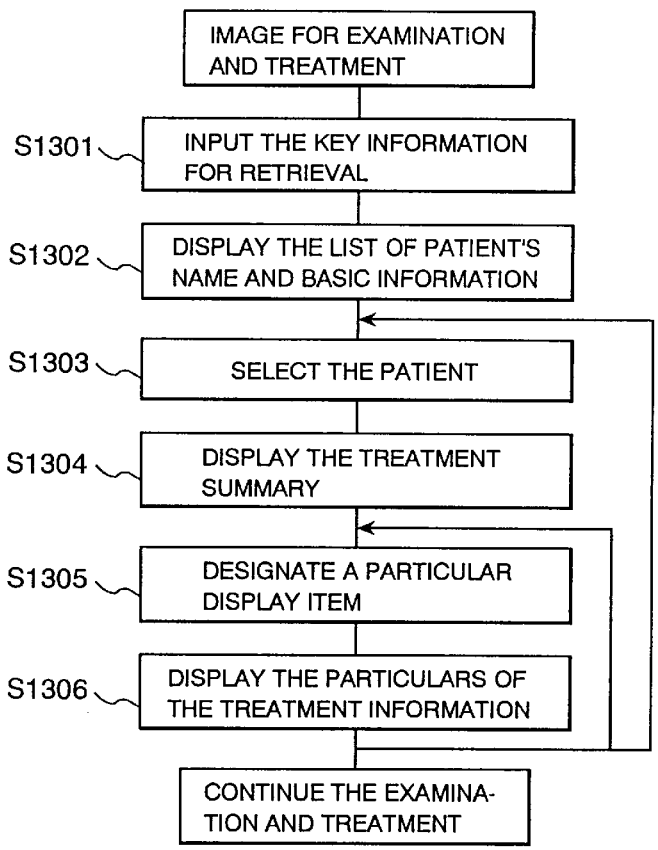

FIG. 19

DATABASE FOR RETRIEVAL  1401

| RETRIEVING KEY | | | | DATA INFORMATION | | |
|---|---|---|---|---|---|---|
| NAME OF DISEASE | ORGAN OF DISEASE | SYMPTOM | ... | PATIENT NO | PATIENT'S BASIC INFORMATION | TREATMENT SUMMARY |

DATABASE FOR TEST RESULT  1402

| RETRIEVING KEY | | | DATA INFORMATION | |
|---|---|---|---|---|
| PATIENT NO | INSPECTION NAME | INSPECTION DATE | INSPECTION ITEM | INSPECTION RESULT GRAPH |

RADIOGRAPH DATABASE  1403

| RETRIEVING KEY | | | DATA INFORMATION |
|---|---|---|---|
| PATIENT NO | INSPECTION NAME | PHOTOGRAPHED DATE | IMAGE DATE |

FIG. 20

```
* * * CASE DB RETRIEVAL * * *
    1. NAME OF DISEASE ( · · · · · · · · · · · )
    2. ORGAN OF DISEASE ( · · · · · · · · · · · )
    3. SYMPTOM ( · · · · · · · · · · · )
```

| SELECTION | PATIENT NO. | PATIENT NAME | SEX | DATE OF BIRTH |
|---|---|---|---|---|
| 11 : | 26-8772-2 | Taro Hitachi | MALE | Jan. 26, 2nd Year of showa |
| 12 : | 27-3872-2 | Hanako Hitachi | FEMALE | Dec. 13, 10th Year of showa |
| 13 : | 29-5663-2 | Jiro Mitsubishi | MALE | Sep. 7, 32nd Year of showa |
| 14 : | 30-4479-2 | Saburo Toshiba | MALE | Mar. 20, 14th Year of showa |
| · | · | · | · | · |
| · | · | · | · | · |
| · | · | · | · | · |

FIG. 21

| TREATMENT SUMMARY | |
|---|---|
| PATIENT  Taro Hitachi   MALE   AGE 54 | TEL  044 (966) 9111 |
| Dr Yoshio Yamada | SPECIAL DISEASE   HIGH BLOOD PRESSURE   DIABETES   OBESITY |
| DISEASE NAME (IN ORDER OF DATE) | PRESCRIPTION, INSPECTION, OPERATION |
| 92/01/23 CHRONIC HEPATITIS<br>·    ·<br>·    ·<br>·    ·<br>·    ·<br>·    · | 92/01/25 CT SCAN OF BODY<br>92/01/26 BLOOD INSPECTION<br>92/01/26 BIOCHEMISTRY INSPECTION  1602<br>·    ·<br>·    · |
| CASE HISTORY | PRESCRIPTION WHEN LEAVING HOSPITAL |
|  |  |
|  | RETURN |

WIDE AREA MEDICAL INFORMATION SYSTEM AND METHOD USING THEREOF

BACKGROUND OF THE INVENTION

1. Field of the Invention

The present invention relates to a wide area medical information system and a method for use thereof by which a patient can receive examination and treatment without going to a doctor at a remote location and more particularly to a wide area medical information system and a method for use thereof by which a patient at any location in the country can receive a remote examination and treatment service from a doctor selected optionally by the patient or can receive various related services from optional medical facilities.

2. Description of the Prior Art

Conventionally, when a patient desires to receive examination and treatment, it is necessary for him to go to a hospital where a doctor is located, for example, even if only for a five minute consultation or queries for diagnosis. Moreover, it is always necessary to wait in a pharmacy or for an accountant for several minutes each time. Another problem is that a patient can go only to a hospital close to his house due to geographical restrictions and cannot select a hospital. Particularly, in a depopulated area such as a remote island, it is difficult to receive satisfactory examination and treatment.

To solve these problems, examination and treatment at home in which a hospital and a patient house are connected electronically to each other via a communication network so that the patient at home can receive examination and treatment services from a doctor working in the hospital has been tentatively tried recently. Specifically, a method for realizing examination and treatment at home is disclosed in Japanese Laid-Open Patent Application No. 3-198832 (Prior art 1) and Japanese Laid-Open Patent Application No. 4-15035 (Prior art 2).

Furthermore, remote examination and treatment services in which a plurality of medical facilities which are located far from each other are connected and information regarding patients including image information is sent and received has been tried experimentally. A medical image transmission system having an image transmission means and reception means for that purpose is disclosed in Japanese Laid-Open Patent Application No. 2-218336 (Prior art 3).

The aforementioned prior arts 1 to 3 realize examination and treatment services from a remote area by the communication process of information using a communication network connecting a patient house and a hospital or hospitals existing at a distance from each other.

However, in the aforementioned prior art, it is difficult to simultaneously select a plurality of doctors for conducting an examination and providing treatment at home or in a remote area by a patient. The reason is that one-to-one connection between a patient house and a predetermined hospital or between specific hospitals is basic. Connection among a plurality of hospitals is also basic. Therefore, it is impossible at all to select a doctor for each clinic section by a patient.

Furthermore, the aforementioned prior art pay attention only to sending and receiving of clinic information between a doctor and a patient or between doctors. Therefore, medical treatment related services to a patient other than examination and treatment are not taken into account.

SUMMARY OF THE INVENTION

An object of the present invention is to realize a wide area medical information system and a method for use thereof by which a patient located in a remote area, for example, in an arbitrary location anywhere in the country can receive remote examination and treatment services of high satisfaction and medical treatment related services other than examination and treatment regardless of the location of the doctor/facilities relative to the patient.

To accomplish this object, the present invention is a wide area medical information system and a method for use thereof comprising a wide area network, a plurality of doctor terminals connected to the wide area network, a plurality of patient terminals connected to the wide area network, and at least one management server connected to the wide area network including an electronic case record file for storing at least clinic information for patients and a doctor database for storing data regarding a plurality doctors registered in the wide area medical information system, wherein the system searches the doctor database on the basis of basic patient information including at least the name of a certain patient input from the patient terminal and patient information including the condition of the patient, selects the corresponding doctor, requests that the selected doctor take charge of examination and treatment for the aforementioned certain patient, registers the correspondence between the approved doctor and the aforementioned certain patient in the electronic case record file, gives the right to access the clinic information regarding the patient for whom the correspondence is registered to the approved doctor, and executes the online examination and treatment including at least queries for diagnosis via the doctor terminal and patient terminal of the doctor and patient in the aforementioned registered correspondence.

In other words, the present invention is established by designating and registering any accessible patient and a plurality of doctors individually by the patient on a wide area network and construct a virtual hospital on the wide area network. Specifically, in the aforementioned hospital system:

(1) correspondence means for making an arbitrarily accessible patient correspond to a plurality of doctors for the patient is installed on the wide area network, and the address of a doctor for the patient or information equivalent to it and the address of the patient for the doctor or information equivalent to it are defined beforehand so as to permit mutual access, and a clinic for executing online examination and treatment from a remote area via this network is provided:

(2) the patient and a pharmacy designated individually by the patient are decided as elements of the wide area network and when the clinic examines the patient, it outputs a prescription to the pharmacy online;

(3) medical facilities other than the clinic designated by the patient individually, for example, various inspection, treatment, and surgical operation facilities are decided as elements of the wide area network and when the clinic examines the patient, it gives various orders to the facilities online;

(4) a financial institution designated by the patient individually is decided as an element of the wide area network, and the clinic asks the financial institution to pay for the treatment for the patient, and the financial institution automatically withdraws the treatment fee from the patient's account; and (5) a management group for managing the whole information processes executed between a patient and a medical facility or between a plurality of medical facilities is installed and centrally manages medical information of each patient generated in a plurality of medical facilities.

According to (1) mentioned above, a patient can select and register a plurality of doctors whose examination and treatment are desired simultaneously, so that he can receive examination and treatment services independent of his/her location relative to the location of the doctor and/or medical facilities.

A patient can select a doctor for each clinic section instead of each hospital. For example, he can designate doctor A in Tokyo for physician and doctor B in Osaka for otolaryngology. Therefore, the patient can receive examination and treatment extending over a plurality of clinic sections and a hospital run for patients can be constructed.

According to (2) mentioned above, a prescription is output to a pharmacy designated optionally by a patient to a doctor in the clinic online. For example, when a patient is at home, a pharmacy which is nearest to his house can be designated and when he is away from home, the nearest pharmacy at that time can also be designated. Namely, a patient can select a method by which he can receive medicine most easily. Therefore, the problem of waiting for extended times before receiving medicine is eliminated.

According to (3), even when a physical inspection or treatment is necessary for a patient, he can receive such measure instructed by a doctor in the clinic in a medical facility designated by him in the same way as with (2).

According to (4), the treatment fee can be withdrawn automatically from the account of a patient. Therefore, the problem of waiting for accounting which is required in a conventional hospital is eliminated.

According to (5), treatment history data of a patient generated in a plurality of medical facilities is integrated and centrally managed, so that superior examination and treatment in terms of consistency and reliability are made possible. For example, side effects caused by taking medicines given from different hospitals and duplicated inspection, which are conventional problems, can be checked. Even when an incurable disease occurs, by searching for a case history database of another patient in the past, it is possible to find a similar case and confer it for examination and treatment.

Furthermore, it is possible to register treatment history data of a new patient having an incurable disease and make use of it for future examination and treatment by sharing such information.

As mentioned above, according to the present invention, not only the clinic but also a plurality of medical facilities designated by a patient are connected electronically to the patient and a virtual hospital is structured on the network. In this case, it functions for the patient as if it is a single hospital information system. Therefore, regardless of where a patient is located, he can receive medical services which are equivalent to those in a hospital in which he would be physically located.

According to the present invention, hereinafter, a hospital constructed virtually on a network by connecting a plurality of optional medical facilities electronically is referred to as "electronic hospital" in a sense of comparison with a hospital in which a patient exists physically.

The foregoing and other objects, advantages, manner of operation and novel features of the present invention will be understood from the following detailed description when read in connection with the accompanying drawings.

BRIEF DESCRIPTION OF THE DRAWINGS

FIG. 7 is a flow chart showing the registration and treatment appointment procedure of the electronic hospital of the present invention.

FIG. 8 is a flow chart showing the procedure of scheduling an actual appointment for examination and treatment with a doctor in the clinic of the electronic hospital, as performed by the patient.

FIG. 9 is a flow chart showing the procedure of executing doctor registration and making a treatment appointment at the same time when examination and treatment are necessary without registering them beforehand.

FIG. 10 is a drawing (No. 1) showing the management table of the electronic hospital of the present invention.

FIG. 11 is a drawing (No. 2) showing the management table of the electronic hospital of the present invention.

FIG. 12 is a drawing (No. 3) showing the management table of the electronic hospital of the present invention.

FIG. 13 is a drawing (No. 4) showing the management table of the electronic hospital of the present invention.

FIG. 14 is a flow chart showing an example of the treatment procedure for a physician of the electronic hospital of the present invention.

FIG. 16 is a flow chart showing the treatment procedure for a surgeon of the electronic hospital of the present invention.

FIG. 17 is a flow chart showing the treatment appointment procedure for a patient having an incurable disease in the electronic hospital of the present invention.

FIG. 18 is a drawing showing an example of the case database of the electronic hospital of the present invention.

FIG. 19 is a flow chart showing an example of the search procedure of the case database of the electronic hospital of the present invention.

FIG. 20 is a drawing showing an example of the search screen of the case database of the electronic hospital of the present invention.

FIG. 21 is a drawing showing an example of the summary screen of the case database of the electronic hospital of the present invention.

DETAILED DESCRIPTION OF THE PREFERRED EMBODIMENTS

The embodiments of the present invention will be explained in detail hereunder with reference to the accompanying drawings.

Figure 1:
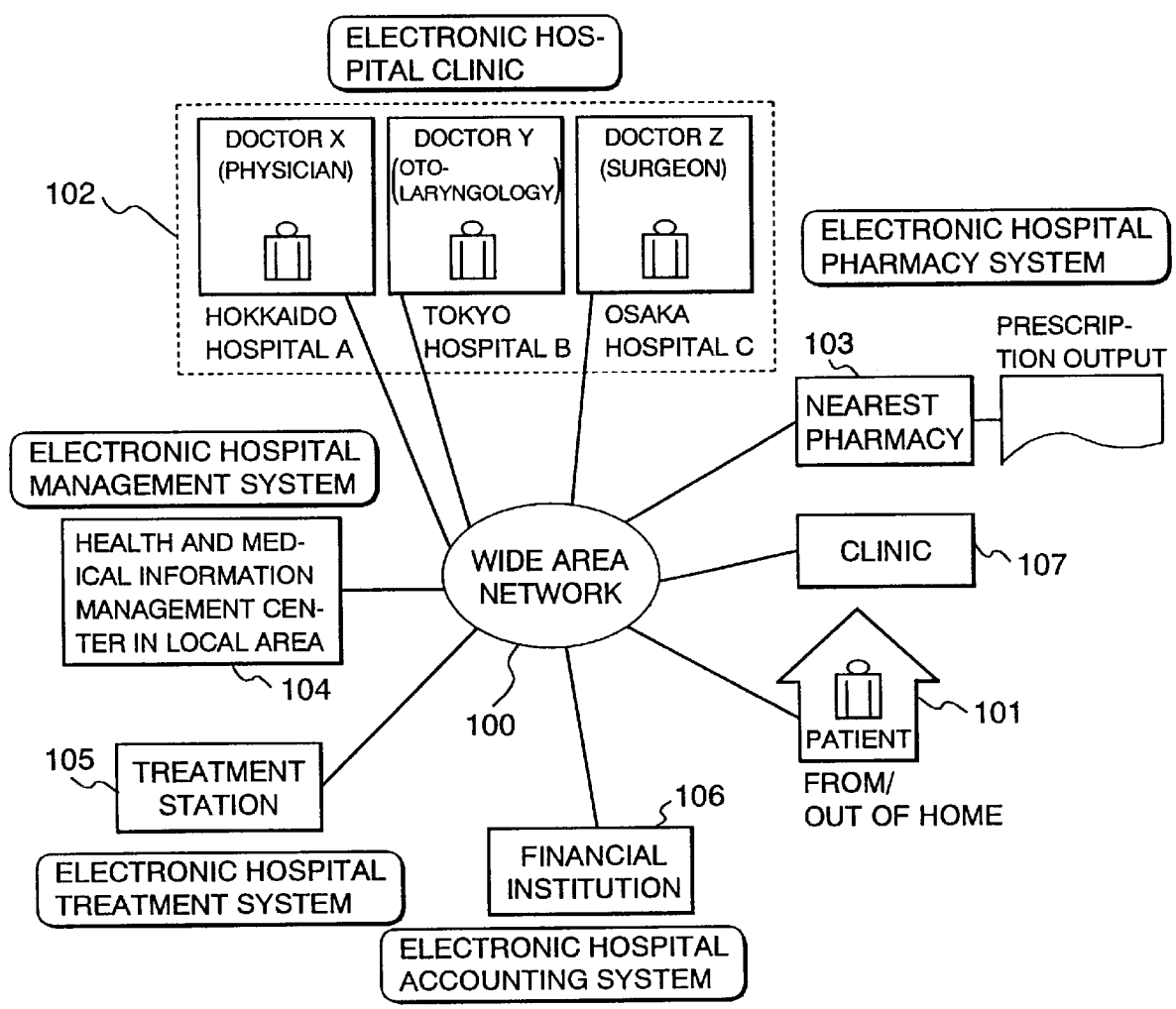
FIG. 1 is a drawing showing an example of the electronic hospital of the present invention.

FIG. 1 shows a constitution example of the electronic system of the present invention. This system is a hospital information system which is virtually constructed on a wide area network with a patient and a plurality of medical facilities being electronically connected. A patient can select an optional medical facility as an element. Via a wide area network 100, a patient side (terminal existing in the patient house or terminal carried by the patient) 101, a clinic 102 comprising a plurality of doctors working at arbitrary locations all over the country, the nearest pharmacy 103 to the patient;s house, a health and medical information management center in a local area (hereinafter abbreviated to only management center) 104 for managing not only treatment history data of all residents in the area where a patient lives (for example, for each prefecture) but also health and medical information at the same time, a treatment station 105 for executing medical services such as examination and treatment for a patient in a city, town, or village where the patient lives, and a financial institution 106 where the deposit account of a patient exists are connected electronically to each other. The electronic hospital system structured by these elements on the network functions for the patient as if it is a single hospital information system. In this system, the clinic 102, the nearest pharmacy to the patient's house 103, the management center 104, the treatment station 105, and the financial institution 106 are similar to the clinic section subsystem, pharmacy subsystem, case record management room, various treatment systems, and accounting system in a conventional hospital information system respectively.

When a patient uses the system, the patient can select optionally only those elements deemed necessary. In this embodiment, a clinic 107 is connected to the patient house 101 and daily examination and treatment at home are executed for a patient. The main function of each element will be explained hereunder briefly.

In this embodiment, the patient 101 receives examination and treatment daily from his family doctor (home doctor) working in the clinic 107. When the patient desires to receive examination and treatment from a more prominent doctor (other than the home doctor) or to be diagnosed by a medical specialist, he utilizes the electronic hospital system. In this case, the patient 101 consults with the home doctor and selects a desired doctor from the doctors registered in this system. Doctors can be selected for each clinic section. Examination and treatment are executed via the wide area network 100. One or more doctors can be selected.

The selected doctor is registered in the clinic 102 of the electronic hospital. FIG. 1 shows an example wherein three doctors in different clinic sections are selected. When each doctor (doctors X to Z) in the registered clinic 102 is accessed from the patient 101, he receives the treatment appointment. The doctor examines the patient on the appointed date via the network 100. For examination and treatment, he confers the treatment history data of the patient 101 managed by the management center 104. The management center 104 always manages the registration relationship between a patient and the clinic 102 and gives the right of accessing the treatment history data of the patient only to the doctor registered in the clinic of the electronic hospital for the patient. By doing this, the privacy of a patient can be protected.

When the doctor in the clinic 102 of the electronic hospital determines that dosage of a drug for a patient is necessary, he performs the following process. The doctor gives an order of prescription to the pharmacy (generally the nearest pharmacy 103 to the patient's house 101) designated by the patient and outputs the prescription online. The pharmacy 103 prepares a medicine according to the output prescription. In this case, on request by the patient, the medicine may be delivered to the patient's house.

When the doctor in the clinic 102 of the electronic hospital determines that physical measures such as examination and treatment are necessary for the patient, he performs the following process. The doctor gives various orders to the treatment center 105 designated by the patient online. Therefore, the patient 101 can receive the necessary measures at the treatment center 105. The treatment center of the present invention is not necessary to be a dedicated one of the electronic hospital. For example, it may be an existing hospital.

Furthermore, the treatment fee is paid as shown below. When the examination and treatment end, the doctor in the clinic 102 asks the financial institution 106 where the patient's deposit account exists to pay the treatment fee to the patient 101. The financial institution 106 automatically withdraws the treatment fee from the deposit account of the patient on the fixed date every month.

The specific hardware and software constitutions of each element are shown hereunder in FIGS. 2, 3, 4, 5, and 6.

Figure 2A:
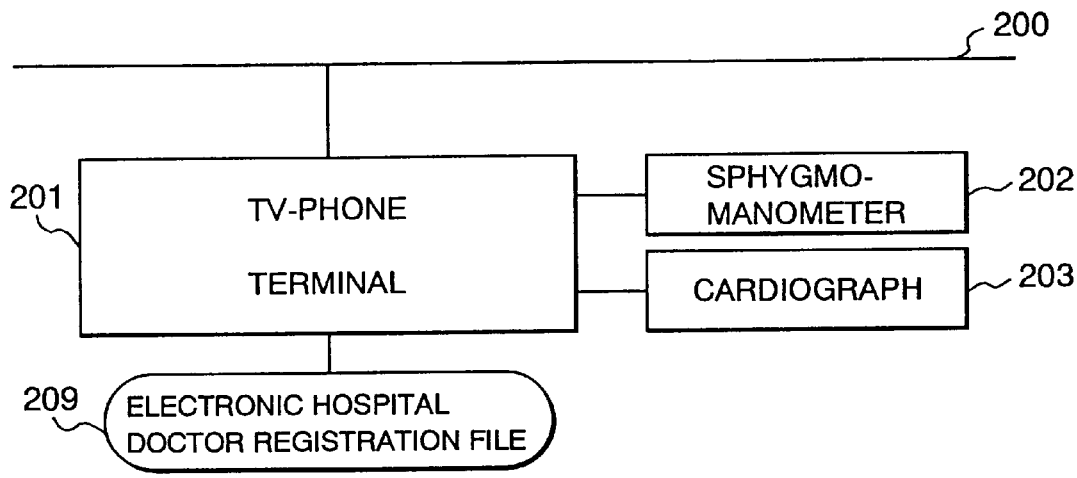
FIGS. 2a, 2b are drawings showing examples on the patient side communicating with the electronic hospital of the present invention.
Figure 2B:
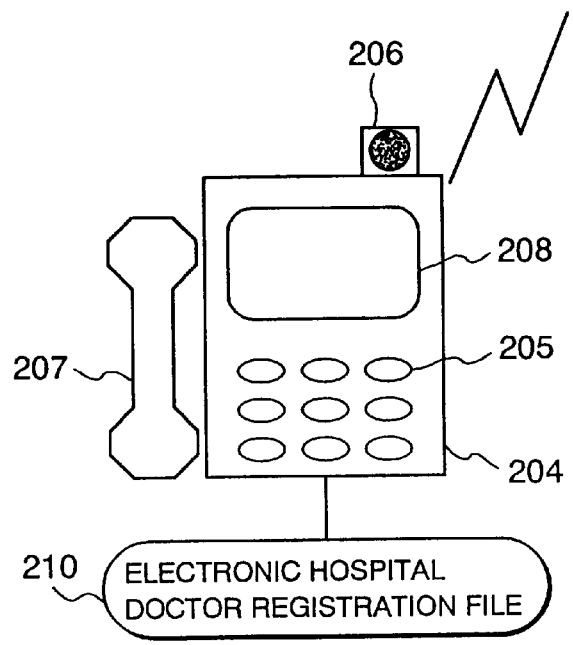

FIG. 2 shows a constitution example of the patient 101. (b) shows a detailed drawing of a TV-phone installed terminal 201 shown in (a). Firstly, (a) will be explained. The TV-phone terminal 201 is installed via a branch network 200 connected to the wide area network 100. Instruments for measuring the body status such as a sphygmomanometer 202 and a cardiograph 203 used for daily health care may be connected to the terminal 201. As another embodiment, there is a constitution available for transmitting data measured by these instruments to a doctor during examination and treatment. This will be described below.

The TV-phone terminal 201 includes an electronic hospital doctor registration file 209 for registering doctors in the clinic 102 of the electronic hospital. A patient communicates with a doctor in the clinic 102 who is registered in the electronic hospital doctor registration file 209 beforehand via the TV-phone terminal 201. The sphygmomanometer 202 and the cardiograph 203 send body information of the patient to the terminal 201 for display thereof and it is used as reference data for examination and treatment.

As another embodiment, the following constitution is available. An embodiment which enables a patient far from home to receive an examination and treatment will be explained. A portable type TV-phone terminal 201 is used. It will be explained by referring to FIG. 2(b) as an example. The-terminal comprises a main body 204, various buttons 205, a miniature TV camera 206, a receiver 207, and a display 208 on the main body. The terminal contains the electronic hospital doctor registration file 209. This terminal communicates with a doctor in the clinic 102 from an arbitrary location via radio.

Figure 3:
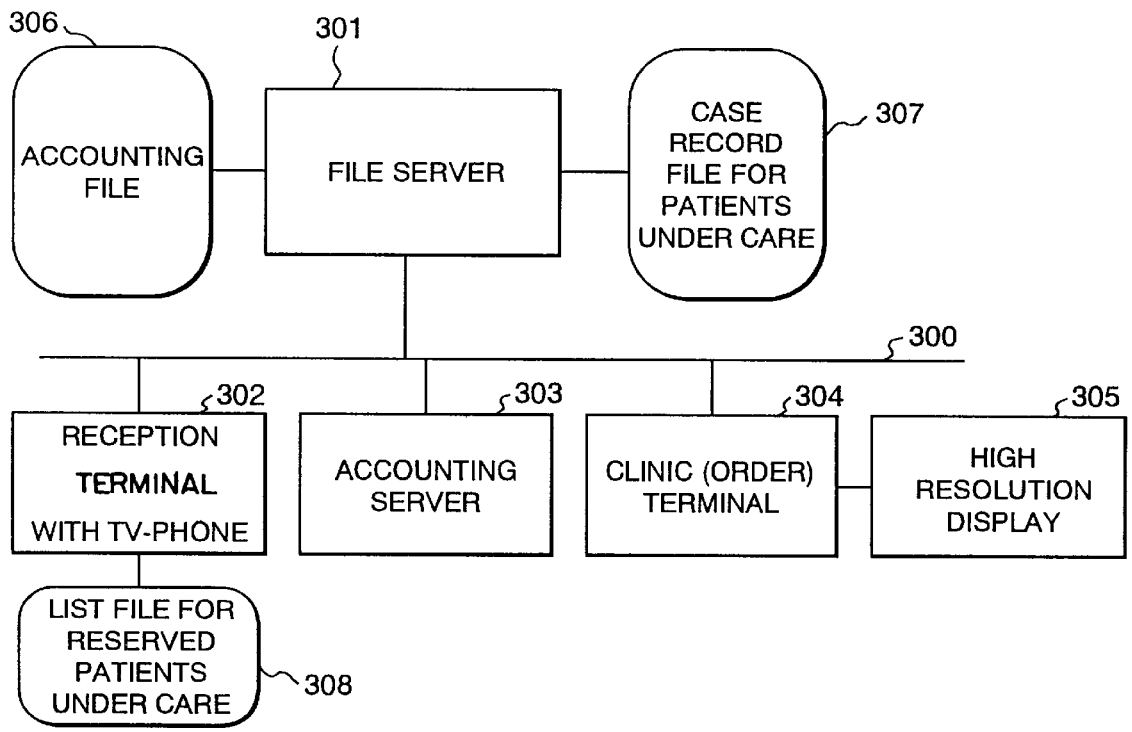
FIG. 3 is a drawing showing an example of the doctor side in the clinic of the electronic hospital of the present invention.

FIG. 3 shows a constitution example of the doctor side 102 constituting the clinic. A file server 301, a reception terminal with TV-phone 302, an accounting terminal 303, a clinic (order) terminal 304, and a high resolution display for image display 305 are connected via a branch network 300 connected to the wide area network 100. The file server 301 has an accounting file 306 and a care record file 307 for storing treatment history information of patients under care who are examined via the network and the reception terminal with TV-phone has a list file for reserved patients under care 308. Each doctor of the clinic receives registration and appointments for examination and treatment from patient's via the reception terminal installed with TV-phone 302.

Basic information such as the patient ID, address, age, and sex for registration and the date of appointment of examination and treatment are registered in the list file for reserved patients under care 308. Prior to examination and treatment, the file server 301 loads down the treatment history data of a patient under care from the management center 104 and stores it in the care record for patients under care.

The clinic terminal 304 downloads the treatment history data of a patient from the file server 301 when necessary and displays it. The doctor advances examination and treatment by interaction with the patient via the TV-phone terminal 201 and by referring to the treatment history data.

The accounting terminal 303 calculates the treatment fee for the treatment content executed by the doctor for the patient and transfers the result to the accounting file 306 in the file server. The data sent to the accounting file 306 is saved by the end of month and used for demand for medical expense payment for the Ministry of Welfare.

Figure 4:
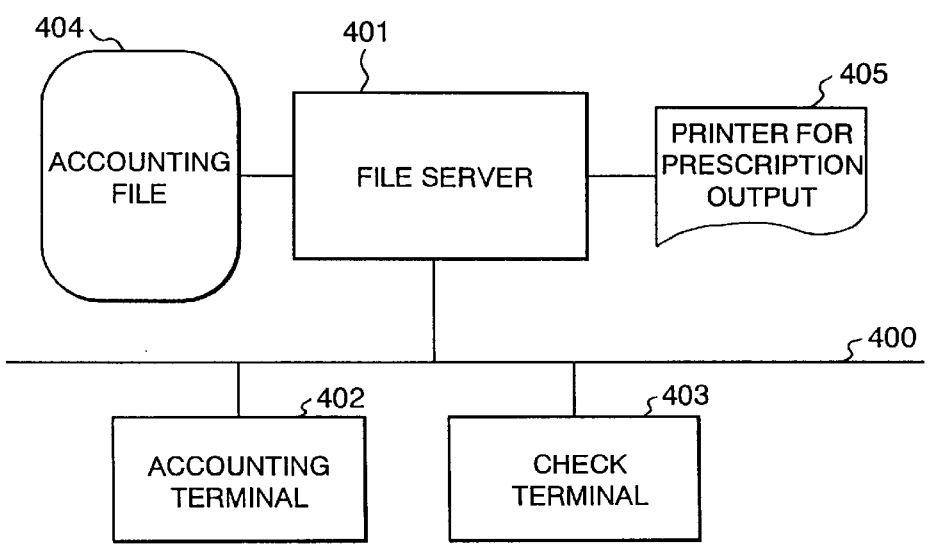
FIG. 4 is a drawing showing an example of the pharmacy side of the present invention.

FIG. 4 shows an example of the pharmacy side 103. A file server 401, an accounting terminal 402, and a check terminal 403 are connected via a branch network 400 connected to the wide area network 100. The file server 401 has an accounting file 404 and is connected to a printer for prescription and medicine pack output 405. The file server 401 receives the prescription order information sent from the clinic 102 and outputs a prescription corresponding to the order content via the printer 405. When the patient comes directly to the pharmacy 103 instead of an instruction of the doctor and attempts to purchase a medicine, the check terminal 403 has a function for conferring the medicine history data of the patient sent from the management center 104 and checks for side effects due to taking of the medicine.

Figure 5:
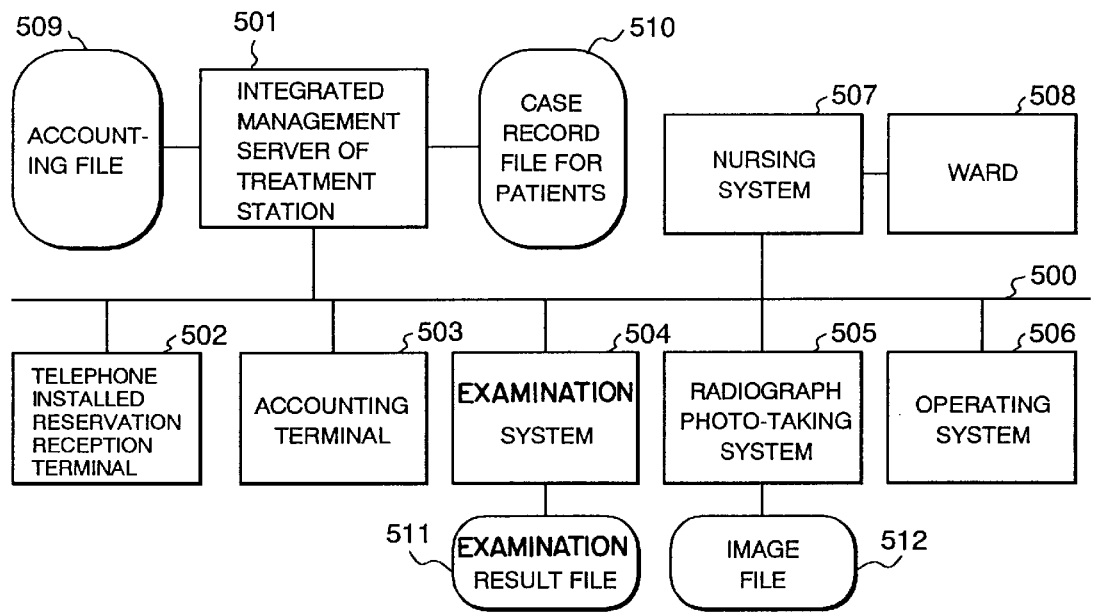
FIG. 5 is a drawing showing an example of the treatment center side of the electronic hospital of the present invention.

FIG. 5 shows an example of the treatment station 105. An integrated management server of treatment station 501, a telephone installed reservation reception terminal 502, an accounting terminal 503, an inspecting subsystem 504, a radiograph photo-taking subsystem 505, an operating subsystem 506, a nursing system 507, and a ward subsystem 508 are connected via a branch network 500 connected to the wide area network 100.

The integrated management server 501 has an accounting file 509. The inspecting system 504 has an inspection result file 511. Furthermore, the radiograph photo-taking subsystem has an image file 512.

The integrated management server receives various order information sent from the clinic 102 and transfers order information to a corresponding subsystem. Each subsystem receiving order information executes a measure corresponding to the order content for the patient. For example, when the order content relates to biochemistry inspection, the order information is sent to the inspecting subsystem 504. In the inspecting subsystem, biochemistry inspection is executed for the patient and the result is stored in the inspection result file 511 and transferred to the management center 104.

The accounting terminal 503 calculates the treatment fee executed for the order and stores the result in the accounting file.

Figure 6:
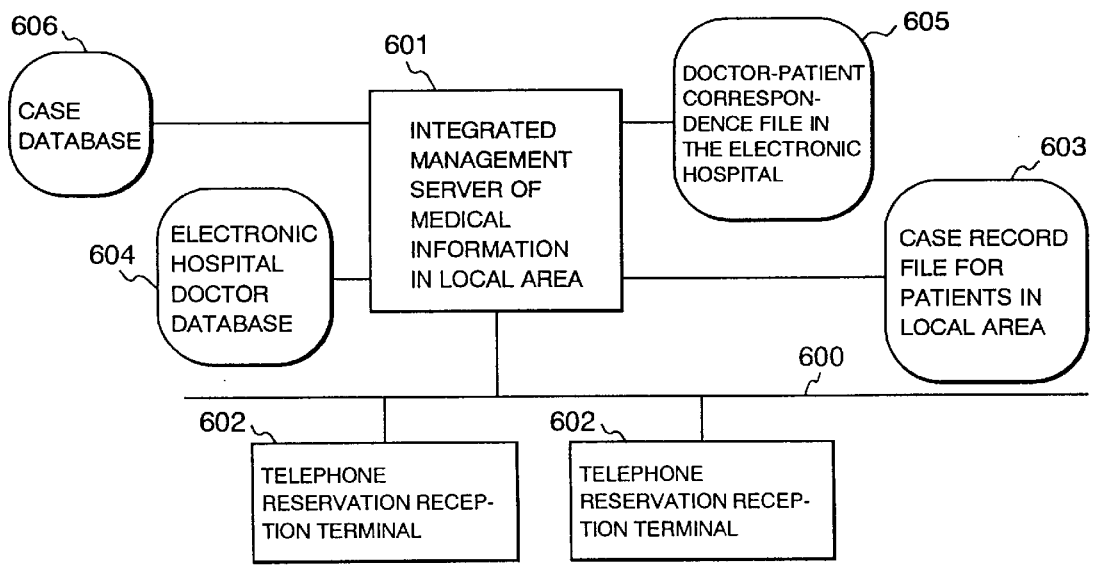
FIG. 6 is a drawing showing an example of the management center side of the electronic hospital of the present invention.

FIG. 6 shows the constitution of the management center 104. The management center monitors the whole electronic hospital and integrates and manages treatment history data of residents in the corresponding local area generated in all medical facilities. An integrated management server of medical information in local area 601 and a plurality of telephone reservation reception terminals 602 are connected via a branch network 600 connected to the wide area network 100.

The integrated management server 601 has a case record file for patients 603 for integrating and managing treatment history information of residents in local area, an electronic hospital doctor database 604 for registering information such as name, place of registration, and special field of each doctor registered beforehand in correspondence with the electronic hospital, a doctor-patient correspondence file in the electronic hospital 605 registering the correspondence between the doctors registered in the electronic hospital and patients thereof, and a case database 606 registering important cases of past patients in the electronic hospital. The integrated management server 601 receives a request of registration in the electronic hospital and treatment appointment from a patient via the telephone installed reservation reception terminal 602, searches the electronic hospital doctor database 604, and introduces a doctor registered in the electronic hospital. When registration is realized between the doctor and the patient, the integrated management server 601 registers the correspondence in the doctor-patient correspondence file in the electronic hospital 605 and gives the right of accessing the treatment history information of the patient stored in the case record file for patients 603 to the doctor. When an incurable disease is diagnosed, the integrated management server 601 gives the right of accessing the case database 606 at the request of the doctor when necessary.

An actual embodiment of the medical information process executed mainly in the electronic hospital will be explained in detail hereafter for each case.

FIG. 7 shows the procedure when the patient side accesses the doctor side via the management center and the patient is registered in the clinic 102 of the electronic hospital by a flow chart. The patient side 101, the management center 104, and the doctor side 102 are as shown in FIGS. 2, 6 and 3 respectively. The registration procedure will be explained hereunder according to the flow chart and each block diagram.

S701: The patient side (for example, the patient 101 and the family doctor in the clinic 107) accesses the management center using the TV-phone terminal 201 installed in the patient's house or the portable TV telephone 204 and notifies it of a request of registration of the patient in the electronic hospital. The management center 104 responds to it via the telephone reservation reception terminal 602.

S702: The management center side 104 asks the patient side 101 about the treatment fee and past case history to be registered and the conditions such as the selection standard of a doctor to be registered and acquires information necessary to introduce a suitable doctor.

S703: The management center side 104 searches the electronic hospital doctor database 604 on the file server 601 from the reception terminal 602 and searches for a doctor in charge for each clinic section under the search condition of case history and desire of the patient. An example of the content of the database 604 is shown in FIG. 10 and it comprises information including the doctor's name, place of registration, section, specialty, history, and others.

S704: A plurality of doctors are generally extracted for each clinic section by searching the database 604, so that they are indicated to the patient.

S705: The patient side selects one or more doctors from the plurality of indicated doctors.

S706: The management center 104 accesses the doctor selected by the patient and requests registration of the patient for the doctor.

S707: The doctor side confers the current list file for reserved patients under care 308 and when there is a room in consideration of the number of patients under care, the doctor side approves reception of registration. When there is no room, the doctor side denies it. If this occurs, the procedure returns to S704.

S7081, S7082, S7083: When the doctor side approves registration of the patient, the management center side 104 registers the doctor and patient in the doctor patient correspondence file in the electronic hospital 605. An example of the content of the file is shown in FIG. 11. At the same time, the right of accessing the electronic case record data of the patient managed by the management center 104 is given to the doctor.

By doing this, the doctor can refer to the case record of the patient. The doctor side registers the basic information such as the patient ID, address, age, sex, and others and the network address for access to the patient from the doctor side in the list file for reserved patients under care 308. An example of the content of the list file for reserved patients under care 308 is shown in FIG. 12.

The patient side registers the doctor ID, doctor's name, clinic section, and network address for access to the doctor side from the patient side in the electronic hospital doctor registration file 209 or 210. An example of the content of the electronic hospital doctor registration file 209 or 210 is shown in FIG. 13.

A series of registration processes from S703 to S7081, S7082, and S7083 is executed for each clinic section whose registration is required by the patient and by doing this, the clinic of the electronic hospital for the patient is structured.

FIG. 8 shows a process example when examination and treatment are appointed if actually necessary for the doctor of the clinic of the electronic hospital registered as mentioned above by the patient side beforehand.

S709: The patient side refers to the electronic hospital doctor registration file 209 or 210 and displays a list of registered electronic hospital doctors on the TV-phone terminal 201 or 204.

S710: The patient side selects a doctor on the terminal according to the current condition of disease.

S711: The patient side refers to the network address registered in the electronic hospital doctor registration file 209 or 210 beforehand and accesses the doctor side via the terminal.

S712, S713: The doctor side and patient side consult with each other directly and decide the first treatment date. The doctor side registers the date in the list file for reserved patients under care 308 and the patient side registers it in the electronic hospital doctor registration file 209 or 210.

The aforementioned example is structured so that a patient makes a contract with a plurality of doctors by introduction of the management center beforehand as mentioned above, forms a personal doctor group, and selects a doctor from those doctors for treatment appointment if necessary. However, there is another constitution available that pre-registration is not executed and registration of a doctor and treatment appointment are executed at the same time when examination and treatment are necessary. A process example in this case is shown in FIG. 9 and the same process as that shown in FIGS. 7 and 8 is executed continuously.

Figure 15:
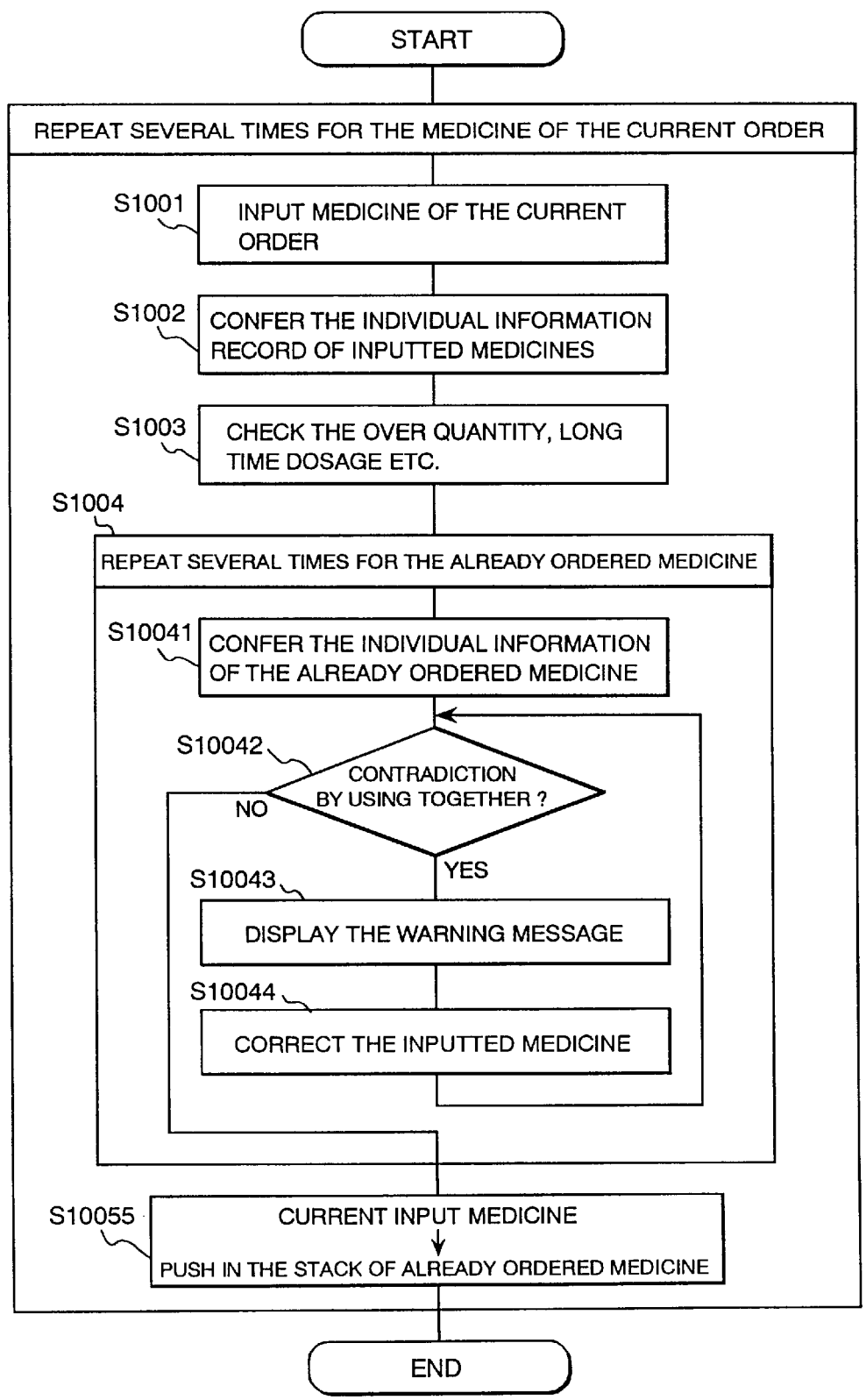
FIG. 15 is a flow chart for explaining the prescription order check algorithm at Step 907.

An embodiment when a patient receives examination and treatment from a doctor in the electronic hospital for whom he finishes treatment appointment as mentioned above will be described hereafter. The embodiment is divided into three cases for explanation such as (a) the patient side receives examination and treatment from a doctor of the electronic hospital and then is given medicine, (b) the patient side receives examination and treatment from a doctor of the electronic hospital and then receives an instruction for various treatments or radiographic photo-taking such as X rays, and (c) when a doctor in the electronic hospital examines a patient, he diagnosis him as having an incurable disease. Flow charts showing the process flow for each case are shown in FIGS. 14, 15, and 16.

FIG. 14 shows a flow chart when the patient side receives examination and treatment from a doctor of the electronic hospital then is given a medicine and it is considered as a typical example of examination and treatment of physician.

This embodiment will be explained hereunder with reference to this flow chart and FIGS. 1, 3, 4, and 6.

S901: On the day before examination and treatment or in the morning of the day, the doctor side of the clinic 102 of the electronic hospital accesses the integrated management server 601 of the management center 104 and loads down the electronic case record data of the patient to be examined to the case record file for patients under care 307 on the file server 301 from the case record file for patients in local area 603 via the wide area network 100.

S902: The patient accesses the doctor according to the treatment appointed date registered beforehand using the TV-phone terminal 201 installed in the patient's house or the portable TV telephone 204. The doctor side receives it by the reception terminal with TV-phone 302.

S903: The doctor side accessed by the patient side loads the case record data of the patient downloaded to the case record file for patients under care 307 on the file server 301 beforehand onto the clinic terminal 304 and displays it.

S904: The doctor asks the patient about the current condition of the disease.

S905: The doctor refers to the case record data. Specifically, the doctor confers the past medicine history and inspection history of the patient and displays the inspection result data on the clinic terminal 304.

S906: As a result of query and reference to the case record data, the doctor gives a diagnosis and inputs the doctor's diagnosis to the case record data.

S907: When the doctor determines that medicinal dosage to the patient is necessary, he issues a prescription order for the patient. The order destination of medicine in this case is the pharmacy (generally the nearest pharmacy of the patient house) 103 designated by the patient beforehand. When the order of prescription is to be issued, it is necessary to check whether the ordered medicine can be taken without trouble and this process is performed at the same time. It will be described later.

S908, S909: When the order issue ends, the doctor shuts the case record of the patient and transfers it to the management center side 104 via the wide area network 100. By doing this, the latest case record data is sent to the management center 104 and when a different doctor examines the patient next, he can use it.

S910: The patient side and doctor side appoint and register the next treatment date. The doctor side registers it in the list file for reserved patients under care 308 and the patient side registers it in the electronic hospital doctor registration file 209 or 210.

S911, S912, S913: On the pharmacy side 103 (generally the nearest pharmacy of the patient house) designated by the patient beforehand, the file server 401 receives the order content issued from the doctor side via the wide area network 100 and outputs the prescription necessary to prepare the ordered medicine and medicine packs for packing medicine to the printer for prescription output 405. Hereafter, the pharmacy performs the medicine preparation process corresponding to the prescription.

The processes from S908 to S910 and from S911 to S913 mentioned above are performed fully independently of each other. When the preparation of medicine at S913 ends, the pharmacy 103 delivers the medicine to the patient house when he desires. By doing this, it is possible for a patient at home to get medicine from a preferred favorite doctor in a remote area.

Next, the algorithm of prescription order check at S907 mentioned above will be explained in detail by referring to the flow chart shown in FIG. 15. When an error message is issued among a series of check processes indicated below, the doctor corrects the order according to the message.

S1001: A message of "Input medicine of the current order" is displayed on the screen of the clinic terminal 304 on the doctor side and the doctor inputs one medicine name of the current order (or medicine code) for it.

S1002: The clinic terminal 304 refers to the individual information of the input medicines. The clinic terminal 304 refers to the individual information of the medicine from the master file of medicines (medicine master) saved in the file server 301.

S1003: The clinic terminal 304 executes the check processes which can be executed only by the individual information of the current input medicines such as the the upper limit of dosage, the long time dosage check for checking the dosage period, etc. and displays a message for the check result.

S1004: The clinic terminal 304 executes the duplicate dosage check for the corresponding input medicine and the already ordered medicine and the concurrent dosage contradiction check for checking side effects caused by taking a plurality of medicines at the same time. The information of the already ordered medicine can be obtained by referring to the medicine history information included in the case record information of the patient and is stored in the memory of the clinic terminal 304 as a stack of the information of previously ordered medicine. The duplicate dosage check and concurrent dosage contradiction check are executed in combination with all of the previously ordered medicines, that is, executed for each of the already ordered medicines. When the checks end, the clinic terminal 304 goes to S1005.

The processes at S1004 will be explained hereunder.

S10041: The clinic terminal 304 checks whether the current input medicine is included in the previously ordered medicines (duplicate dosage check). If it is included, the clinic terminal 304 displays a message notifying duplicate dosage. If this occurs, it is necessary that the doctor corrects the input ordered medicine and inputs a new one. When the duplicate dosage error is eliminated, the clinic terminal 304 goes to S10042.

S10042: The clinic terminal 304 refers to the individual information of the corresponding input medicine and the individual information of one medicine in the stack of already ordered medicines from the medicine master of the file server 301.

S10043: The clinic terminal 304 decides whether the concurrent dosage contradiction relation is realized between the two medicines according to the contradiction information content registered in each individual patient's information.

S10044: When the result of S10043 is decided as concurrent dosage contradiction, the clinic terminal 304 displays a warning message and goes to S10045. Otherwise, the clinic terminal 304 returns to S10041 and checks the corresponding input medicine and the next ordered medicine. Namely, the clinic terminal 304 refers to the next individual information in the already ordered medicine stack and executes the same process.

S10045: The clinic terminal 304 corrects the order input and reinputs a new order and returns to S10041.

S1005: Assuming that the check for the corresponding input medicine and all of the previously ordered medicines ends normally, the clinic terminal 304 adds the corresponding input medicine to the top of the conventional already ordered medicine stack as a previously ordered medicine.

When S1005 ends, the clinic terminal 304 returns to S1001 and repeats the aforementioned series of processes for the next corresponding input medicine. The clinic terminal 304 repeats S1001 to S1005 for each of the current ordered medicines and when the check for all the current ordered medicines ends, the clinic terminal 304 ends the processes.

By the aforementioned series of processes, the check for prescription order is executed. The medicine history information of previously ordered medicines to be conferred for checking in the series of processes is based on the case record data of patient managed by the management center 104 centralizedly and it includes information of medicines dosed for the same patient in all the medical facilities. Therefore, it is possible to check for side effects caused by taking medicines given from different medical facilities at the same time, which is a conventional problem. In the above example, it is assumed that the doctor side executes the prescription order check. However, when a patient purchases a medicine directly from the pharmacy 103, it is necessary that the pharmacy side executes the check. In this case, the pharmacy side 103 refers to the medicine information of the patient of the management center 104 and the check terminal 403 on the pharmacy side executes the same check process.

FIG. 16 shows a flow chart when the patient side receives examination and treatment from a doctor of the electronic hospital and then receives an instruction of various treatments or radiographic photo-taking such as X rays and examination and treatment by a surgeon are assumed. In this case, when the examination and treatment end, it is necessary that the patient receives those measures in the nearest treatment station. The examination and treatment will be explained hereunder by referring to this flow chart and FIGS. 1, 5, and 6.

S1101: On the day before examination and treatment or in the morning of the day of treatment, the doctor side 102 accesses the integrated management server 601 of the management center 104 and downloads the case record data of the patient to the case record file for patients under care 307 on the file server 301 from the case record file for patients in local area 603 via the wide area network 100.

S1102: The patient accesses the doctor according to the treatment appointed date using the TV-phone terminal 201 installed in the patient's house or the portable TV telephone 204.

S1103: The doctor side accessed by the patient side opens the case record data of the patient downloaded to the case record file for patients under care 307 on the file server 301 beforehand and displays it on the clinic terminal 304.

S1104: The doctor asks the patient about the current condition of the disease.

S1105: The doctor refers to the case record data of the patient and the image data. Specifically, the doctor refers to the past medicine history and inspection history of the patient and displays the inspection data on the clinic terminal 304 and the image data on the high resolution display 305.

S1106: The doctor executes various image processes such as gradation conversion, filtering, and others on the high resolution display 305 and reads images.

S1107: As a result of query and reference to the image data, the doctor gives a diagnosis and explains the result for the patient.

S1108: The doctor inputs the image read report and doctor's diagnosis to the case record data.

S1109: The doctor issues an order of necessary treatments and radiograph photo-taking to the treatment station 105 (generally in a city, town, or village where the patient lives) designated by the patient beforehand and also indicates it to the patient. It is not necessary that the treatment station is dedicated to the electronic hospital and for example, the facility of an existing hospital may be used.

S1110, S1111, S1112: When the order issue ends, the doctor shuts the case record of the patient and transfers it to the management center side 104 via the wide area network 100. The integrated server 501 receives the order content issued from the doctor side via the wide area network 100 and the treatment station 105 transfers it to each subsystem, for example, the nursing system 507 and the radiograph photo-taking system 505.

S1113: The patient side and doctor side appoint and register the next treatment date. The doctor side registers it in the list file for reserved patients under care 308 and the patient side registers it in the electronic hospital doctor registration file 209.

The current examination and treatment end at S1113 and hereafter the processes such as treatment and inspection for the patient which are to be executed mainly by the treatment station 105 are executed.

S1114: The patient arrives at the treatment station 105. This occurs after the aforementioned examination and treatment are executed but it is not limited to the treatment date.

S1115: Various processes, radiography, etc. corresponding to the order contents of the doctor are executed for the patient. The image data imaged by the radiograph photo-taking system 505 is stored in the image file 512 in the subsystem once.

S1116: The image data of the patient is transferred to the integrated management server 501 from the image file 512 and to the management center 104 via the wide area network.

S1117: The management center 104 preserves the image data sent from the treatment station 105 in the record file for patients in local area 603 together with the case record of the patient.

By doing this, the latest image data for the next treatment can be used.

FIG. 17 is a flow chart showing a treatment example when a patient is examined by a doctor of the electronic hospital and diagnosed as having an incurable disease. In this case, it is generally difficult to give a suitable diagnosis only by the case record data of the patient under treatment at present. Therefore, in this case, the doctor examines the patient by referring to the case database 606 collecting past cases of other patients preserved in the management center 104. The examination and treatment will be explained hereunder by referring to this flow chart and FIGS. 1, 5, and 6.

S1201: On the day before examination and treatment or in the morning of the day of treatment, the doctor side 102 accesses the integrated management server 601 of the management center 104 and downloads the case record data of the patient to the case record file for patients under care on the file server from the case record file for patients in local area 603 via the wide area network 100.

S1202: The patient accesses the doctor according to the treatment appointed date using the TV-phone installed terminal 201 in the patient's house or the portable TV telephone 204.

S1203: The doctor side accessed by the patient side opens the case record data of the patient downloaded to the case record file for patients under care 307 on the file server 301 beforehand and displays it on the clinic terminal 304.

S1204: The doctor asks the patient about the current condition of the disease.

S1205: The doctor refers to the case record data and the image data. Specifically, the doctor refers to the past medicine history and examination history of the patient and displays the examination data on the clinic terminal 304 and the image data on the high resolution display 305.

S1206: The doctor executes various image processes such as gradation conversion, filtering, and others on the high resolution display 305 and reads images.

S1207: As a result of query and reference to the image data, the doctor gives a diagnosis of an incurable disease. If this occurs, the doctor notifies the management center 104 immediately and requests an access right to the case database 606 on the integrated management server 601. The management center 104 receiving it gives the access right to the case database 606 to the doctor immediately.

S1208: The doctor obtaining the access right downloads the case database 606 from the management center side 104 via the wide area network 100 and stores it in the case record file for patients under care 307 on the file server 304.

S1209, S1210: The doctor inputs the symptom of the patient under treatment at present and retrieves the case database 606.

S1211: As a result of reference to the case database 606, the doctor gives a diagnosis.

S1212: The doctor inputs the doctor's diagnosis to the case record data and describes an incurable disease in the case record. By doing this, the case history data of the patient under treatment at present is registered in the case database 606 as the latest data.

S1213: As a result of the above diagnosis, the doctor issues an order of necessary treatments and inspection to the treatment station 105 designated by the patient beforehand and so informs the patient.

S1214, S1215, S1216: When the order issue ends, the doctor shuts the case record of the patient and transfers it to the management center side 104 via the wide area network 100.

The integrated server 501 receives the order content issued from the doctor side via the wide area network 100 and the treatment station 105 transfers it to each subsystem, for example, the nursing system 507 and the inspecting system 504.

S1217: The patient side and doctor side appoint and register the next treatment date. The doctor side registers it in the list file for reserved patients under care 308 preferentially to other patients. On the other hand, the patient side registers it in the electronic hospital doctor registration file 209. The examination and treatment at each time end at S1217 and hereafter the processes such as treatment and inspection for the patient which are to be executed mainly by the treatment station are executed.

S1218: The patient arrives at the treatment station. This occurs after the aforementioned examination and treatment are executed but it is not limited to the treatment date.

S1219: Various processes, radiography, etc. corresponding to the order contents of the doctor are executed for the patient. The examination result data executed by the examination subsystem is stored in the examination result file 511 once.

S1220: The examination result data of the patient is transferred to the integrated management server 501 from the inspection result file 511 and to the management center 104 via the wide area network.

S1221: The management center 104 preserves the examination result data sent from the treatment station in the case record file for patients in local area 603 together with the case record of the patient.

The characteristic of the aforementioned embodiment is the retrieval process of S1109 and S1110 of the case database 606. It will be explained in detail hereunder by referring to FIGS. 18, 19, 20, and 21.

FIG. 19 shows the internal structure of the case database 606 of the present invention. The database comprises a database for case retrieval 1401 and databases for various results such as inspection and radiographic image (a database for test result 1402 and a database for radiographic image 1403). Data is downloaded to the case record file for patients under care 307 on the file server 301 on the patient side 102 from the management center 104 via the wide area network 100.

The database for case retrieval 1401 holds a plurality of retrieval informations such as disease name, disease location, symptom, etc. as key information and holds patient number, patient basic information, and clinic summary as data information. The key information includes characteristics such as disease name, disease location, symptom, etc. which are extracted from the doctor's diagnosis of each examined patient and input by a doctor himself as code information or which are selected and input from the retrieval key menu indicated beforehand. The clinic summary information is summary information of clinical progress such as prescription, examination, operation, etc. and the summary when an inpatient leaves the hospital is a typical one.

The databases for various results 1402 and 1403 hold the results of examination and radiograph photo-taking of past real patients or doctor's diagnosis information for them for each patient and have the patient number or patient name as a retrieval key. When a doctor retrieves the aforementioned case database, he retrieves the database for case retrieval 1401 using the disease name, disease location, symptom, etc. as a retrieval key first and obtains rough information regarding past patients having the same symptom on the clinic terminal 304. Thereafter, if necessary, he retrieves the databases for various results 1402 and 1403 of those patients by each patient number, etc. and displays more detailed information on the clinic terminal 304.

FIG. 18 is a flow chart showing the procedure of retrieval and display of the care database 606 of the present invention. This procedure is executed when at S1209 to S1211 shown in FIG. 12, that is, the treatment action is executed, the disease of a patient is diagnosed as being an incurable disease and the treatment data of a past real patient having a similar case to that of the patient under treatment is retrieved by using the case database in the management center 104.

S1301: Firstly, the doctor inputs a plurality of retrieval informations such as disease name, disease location, symptom, etc. expressing characteristics of the symptom of the patient under treatment. These retrieval informations are inputted directly by the doctor or selected and input from the retrieval menu indicated beforehand.

S1302: The clinic terminal 304 searches the database for care retrieval 1401 from the input retrieval informations and displays a list of patient name and patient basic information of the corresponding patient. An example of the display screen in this case is shown in FIG. 20.

S1303: The doctor confirms the selected patient list on the screen and selects one from the patients displayed in the list.

S1304: The clinic terminal 304 receiving it extracts the treatment summary of the selected patient from the database for care retrieval 1401 and displays it on the screen. The treatment summary is treatment summary information such as prescription, inspection, radiograph photo-taking, etc. which is represented by the summary when an inpatient leaves the hospital and an example of the display screen is shown in FIG. 21.

S1305: The doctor refers to the aforementioned output screen and when there is treatment information to be displayed more in detail, he designates the item (for example, detailed contents of the biochemistry inspection) on the screen. The display item is designated by clicking the displayed item directly like 1602 shown in FIG. 21.

S1306: When the aforementioned item requiring display of detailed contents is selected, the clinic terminal 304 retrieves the database for various results (for example, the database for retrieval result) of the corresponding patient by the patient number or patient name and displays the designated detailed information on the screen. Thereafter, when there is another item to be referred to, the clinic terminal 304 returns to S1305. When the clinic terminal 304 desires to refer to the case of another patient, it returns to S1303.

By searching the case of a past patient having the similar condition of the disease to a patient of incurable disease under treatment like this, a doctor can obtain various reference data, so that he can give a precise diagnosis. In a conventional single hospital, it is difficult to acquire such an important case as a database. However, the electronic hospital of the present invention integrates and manages patient data from all medical facilities, so that it is possible. The treatment record of a patient of incurable disease newly generated is registered in the case database 606, so that it can be used for future examination and treatment and can contribute to advance of medicine.

According to the present invention, a patient can receive examination and treatment from a plurality of doctors working at arbitrary medical facilities all over the country without depending on the location where he exists, so that examination and treatment of higher quality can be executed. Since a patient can construct a hospital for himself by selecting a doctor for each clinic section, the reliability and satisfaction of the patient for examination and treatment are extremely improved. In addition, services other than examination and treatment such as issue of a prescription can be received from a facility designated by the patient side via online wide area medical information communication from the clinic, so that there is an advantage that the labor and time consumption of a patient can be reduced extremely in comparison with the conventional hospital system. Furthermore, by centrally managing treatment history data of all patients and using it for examination and treatment, it is possible to check various orderings precisely and indicate plentiful similar case data even when an incurable disease occurs.

The invention claimed is:

1. A wide area medical information system, comprising:

a wide area network;

a plurality of doctor terminals connected to said wide area network;

a plurality of patient terminals connected to said wide area network;

at least one management server connected to said wide area network including an electronic case record file for storing therein at least clinic information for patients and a doctor database storing therein data for a plurality of doctors registered as members in said wide area medical information system;

means for searching for a doctor corresponding to a certain patient utilizing said doctor database on the basis of basic patient information input from one of said patient terminals including at least the certain patient's name and patient information including the condition of the certain patient;

means for requesting that the doctor found by said searching means take charge of examination and treatment of the certain patient;

means for registering, when the doctor accepts the request of said requesting means, the correspondence between the doctor and the certain patient in said electronic case record file;

means for giving the right to access the clinic information of the certain patient for which said correspondence is registered to the doctor; and means for executing an online examination and treatment including at least queries for diagnosis via said doctor terminal and patient terminal of the doctor and the certain patient having said registered correspondence.

2. A wide area medical information system according to claim 1, further comprising:

a plurality of pharmacy terminals connected to said wide area network; and means for transmitting online a prescription order and a prescription for the certain patient to at least one pharmacy terminal of a specific pharmacy designated by the patient among said plurality of pharmacy terminals online by the doctor.

3. A wide area medical information system according to claim 1, further comprising:

a plurality of treatment station terminals connected to said wide area network for executing various inspections and treatments for patients; and means for sending a treatment order for the certain patient to at least one specific treatment station terminal designated by the certain patient among said plurality of treatment station terminals online by the doctor.

4. A treatment method in a wide area medical information system including a wide area network, a plurality of doctor terminals connected to said wide area network, and a plurality of patient terminals connected to said wide area network, said method comprising the steps of:

searching for a doctor corresponding to a certain patient utilizing a doctor database on the basis of basic patient information input from one of said patient terminals including at least the name of a certain patient and patient information including the condition of the certain patient;

requesting that the doctor found by said searching step take charge of examination and treatment of the certain patient;

registering, when the doctor accepts the request, the correspondence between the doctor and the certain patient in the electronic case record file;

giving the right to access the clinic information of the certain patient for which said correspondence is registered to the doctor; and executing an online examination and treatment including at least queries for diagnosis via said doctor terminal and patient terminal of the doctor and the certain patient having said registered correspondence;

wherein said electronic case record file and doctor database are at least an electronic case record file for storing therein at least treatment information for patients and a doctor database recording therein data for a plurality of doctors registered in said wide area medical system and are installed in at least one management server connected to said wide area network.

5. A management server connected to a medical information system, comprising:

an electronic case record file storing at least clinic information for patients;

a doctor database storing data for doctors registered as members in said medical information system;

means for searching for a doctor corresponding to a certain patient, by utilizing said doctor database on the basis of basic input patient information including at least the patient's name and the condition of the certain patient;

means for requesting that the doctor takes charge of examination and treatment for the certain patient;

means for registering the correspondence between the approved doctor and the certain patient in said electronic case record file;

means for giving the right to access the clinic information of the certain patient for which said correspondence is registered to the doctor; and means for executing an online examination and treatment by said approved doctor to the corresponding patient, including at least queries for diagnosis of the certain patient.

* * * * *